(12) United States Patent
Klotz et al.

(10) Patent No.: US 8,114,042 B2
(45) Date of Patent: Feb. 14, 2012

(54) ORTHOTIC LIFT APPARATUS

(76) Inventors: Dell Klotz, Houston, TX (US); James M Killian, Houston, TX (US)

( * ) Notice: Subject to any disclaimer, the term of this patent is extended or adjusted under 35 U.S.C. 154(b) by 251 days.

(21) Appl. No.: 12/456,678

(22) Filed: Jun. 19, 2009

(65) Prior Publication Data

US 2010/0324463 A1 Dec. 23, 2010

(51) Int. Cl.
*A61F 5/00* (2006.01)
*A41D 13/00* (2006.01)

(52) U.S. Cl. .............................. 602/28; 2/467

(58) Field of Classification Search .............. 602/1, 5, 602/23, 27, 28, 29; 128/882; D24/190–192; 2/44, 467; 482/79, 122, 124
See application file for complete search history.

(56) References Cited

U.S. PATENT DOCUMENTS

| | | |
|---|---|---|
| 2,439,100 A | 4/1948 | Richards |
| 3,976,059 A | 8/1976 | Lonardo |
| 3,986,501 A | 10/1976 | Schad |
| 4,289,122 A | 9/1981 | Mason et al. |
| 4,329,982 A | 5/1982 | Heaney |
| 4,459,980 A | 7/1984 | Perser et al. |
| 4,554,912 A | 11/1985 | Haberman |
| 4,817,589 A | 4/1989 | Wertz |
| 5,112,296 A | 5/1992 | Beard et al. |
| 5,215,508 A * | 6/1993 | Bastow ........................ 482/79 |
| 5,219,324 A | 6/1993 | Hall |
| 5,257,969 A | 11/1993 | Mance |
| 5,269,748 A | 12/1993 | Lonardo |
| 5,277,699 A * | 1/1994 | Williamson ................... 602/28 |
| 5,382,224 A * | 1/1995 | Spangler ....................... 602/23 |
| 5,603,692 A | 2/1997 | Maxwell |
| 5,878,748 A | 3/1999 | Garth et al. |
| 5,897,520 A | 4/1999 | Gerig |
| 6,102,881 A | 8/2000 | Quackenbush et al. |
| 6,267,742 B1 | 7/2001 | Krivosha et al. |
| 6,361,517 B1 | 3/2002 | Slinger |
| 6,592,539 B1 * | 7/2003 | Einarsson et al. ............. 602/62 |
| 6,602,217 B2 | 8/2003 | Crawford et al. |
| 6,648,843 B1 | 11/2003 | Marciano et al. |
| 6,790,165 B2 * | 9/2004 | Huang ............................ 482/79 |
| 7,125,392 B2 | 10/2006 | Scott |
| 7,354,413 B2 | 4/2008 | Fisher |

* cited by examiner

*Primary Examiner* — Patricia Bianco
*Assistant Examiner* — Tarla Patel
(74) *Attorney, Agent, or Firm* — Gary L. Bush; Taylor P. Evans; Andrews Kurth LLP

(57) ABSTRACT

An orthotic apparatus for assisting a person having an orthotic disability, such as foot drop, comprising an ankle belt component and a shoe/foot belt component connected by a pair of coil springs which are adjustably and releaseably attached between the belts. The foot at the beginning and end of the step will flex, due to the springs, and still return to lift the foot, which allows for normal walking and requires no special adaptation to the shoe.

21 Claims, 3 Drawing Sheets

ORTHOTIC LIFT APPARATUS

BACKGROUND OF THE INVENTION

1. Field of the Invention

This invention relates to an apparatus designed to assist a person with focal limb weakness, in particular those having a foot-drop type of disability with weakness or paralysis of dorsiflexion and eversion of the foot and extension of the toes. In particular the present foot drop aid is quickly and easily attached on the foot or shoe and onto the leg of the patient employing reliable, long use coil springs for the motive force.

Persons who have sustained a stroke, peripheral nerve injury, or suffer from diseases such as multiple sclerosis, et al., generally incur certain neuromuscular pathological conditions because of damage to the nerves which innervate the muscles involved. This damage occurs centrally in the brain and/or spinal cord, or locally to peripheral nerves, such as those found in the leg, resulting in paralysis or partial paralysis in varying degrees of severity to different parts of the body. Generally, the distal joints are proportionately weaker than the more proximal joints (proximal meaning close to the midpoint of the body). Foot-drop is characterized in that a person, who otherwise has sufficient muscular control to move his foot relative to his ankle in plantar flexion (a downward push off motion), lacks sufficient muscular control to subsequently effect a dorsiflexion motion to raise the foot back up for the next step. Also usually evidenced in persons having foot-drop is the diminished capacity to move the foot in what is termed eversion, or rotating the outer part of the foot in an upward manner.

Paralysis, in any degree, of the ankle and the mid-tarsal joint (just distal to the ankle), and the resultant foot-drop, present greater problems because of the independent movement required of them in walking. Ankle motions are dorsiflexion (up) and plantar flexion (down), and mid-tarsal joint motions are inversion (inward turning) and eversion (outside edge of the foot turned up). Paralysis or partial paralysis for any of the reasons described herein usually impair the ankle and mid-tarsal joint such that dorsi-flexion and eversion are weaker than plantar flexion and inversion. Where a foot-drop problem is present, walking without the assistance of a brace or support will result in the front (toe) portion of the foot dragging along the ground after the leg and foot have completed the plantar flexion portion of the gait. Therefore, a need exists for a foot-assist mechanism which selectively provides dorsiflexion support for the foot by compensating for the weakened muscles while allowing the functioning flexor muscles or portions thereof to continue to contract to their fullest extent.

2. Related Art

A number of devices have been provided to date to alleviate foot-drop which includes short-leg braces having metal uprights, metal stirrups, molded calf cups, etc. Rigid devices such as U.S. Pat. No. 3,986,501 to Schad are static in nature in that they maintain the foot in a relatively fixed position in relation to the leg (which is never greater than 90 degree.) at all times so that the entire lower leg from calf to toes moves en masse as a rigid structure being propelled and supported by the person's knee, hip and spine, thereby producing an awkward gait and immobilize working muscles to a degree, contributing to disuse atrophy or earlier degeneration.

More recently several devices which will aid the functioning of those muscles directly effected by a disabling condition, such as those described hereinbefore, but which allows full range of motion of the foot and usage of those muscles either not effected or only partially effected, such as described in U.S. Pat. Nos. 4,817,589; 5,257,959; 6,602,217 and 7,354,413 have employed elastomeric components for foot lift. The '959, '217 and '413 devices required attachment directly on the foot while the '217 device requires special attachment means on a shoe.

It is an advantage of the present invention as it relates to a foot lit apparatus that in addition to allowing full range of motion of the foot and usage of those muscles either not effected or only partially effected, that it provides a more reliable and longer use foot lift component. It is a further advantage of the present foot lift device that is easily attached by the patient directly to the foot for use with a shoe or directly onto any shoe worn by the patient.

Finally, it is intended to provide a foot-drop assist device which is lightweight, relatively inconspicuous, easy to use, and very inexpensive to make and maintain.

A person having a foot-drop type disability wearing the present foot lift apparatus can use relatively unaffected muscles without hindrance or discomfort to their fullest extent, e.g., by extending the foot (plantar flexion), while at the same time enjoying the benefits of a convenient selectively-active assist mechanism which will help them to walk normally. The present foot lift device is particularly useful to stroke victims since the muscles used to raise the foot (dorsiflexion) and turn it outward (eversion), both of which are required in walking, are nearly always affected by those persons suffering residual paralysis as a result of a stroke.

SUMMARY OF THE INVENTION

In accordance with the present invention, there is provided an apparatus for assisting a person having an orthotic weakness comprising a first belt having two ends, a hooks/loops component on a first side at a first end of said first belt and a cooperating hooks/loops component on a second side of said first belt distal to said first end; a pair of first brackets spaced apart and attached to said first side of said first belt, a pair of coil springs attached to one each of said first brackets; a second belt having two ends, a hooks/loops component on a first side of said second belt at a first end and a cooperating hooks/loops component on a second side of said second belt distal to said first end; a pair of second brackets spaced apart and attached to one side of said second belt; and two adjustable straps attached one each to said springs and attached one each to said second brackets in operable alignment with one each said springs.

One embodiment of the present invention is an apparatus for a foot-drop type disability which includes an ankle attachment member, a pair of coil springs attached to the ankle attachment member, a shoe belt for attaching around the wearer's shoe or foot forward of the ball of the foot and a pair of adjustable, releaseable straps affixed from a shoe belt having attachment means to one each of the coil springs. When the apparatus is in use, the ankle belt is attached at or immediately above the ankle, the coil spring contracts to raise the wearer's foot during the time period that the wearer is not forcibly extending the strap by downwardly extending his or her foot. In its preferred embodiment, the present apparatus is extremely easy to put in use since the ankle belt and the shoe belt are attached around the ankle and the shoe by adjustable, releaseable straps, such as hooks and loops (VELCO™) and the two belts are connected by engagement of the two straps. The present foot-drop assist apparatus therapeutically aids progressively debilitating diseases such as multiple sclerosis by permitting the viable muscles to remain fully active until they are directly effected by the damaging disease.

For a better understanding of the present invention, together with other and further advantages, reference is made to the following description, taken in conjunction with the accompanying drawings. Like reference characters designate like parts in the drawings. In some instance there may be reversal of parts that result in the same functionality.

The present apparatus is designed for functionality, easy of manufacturing with readily available, inexpensive materials and having minimum obtrusive appearance obtained by its low positioning on the leg of the user. By leaving the ankle belt and the shoe belt connect, the simple two step attachment procedure allows the user to attach the apparatus at night with or without shoes and with reduced light.

DESCRIPTION OF THE INVENTION

The device may be viewed as having two parts. 1) An ankle cuff with soft foam inside, two springs, each spring with an adjusting strap made up of a hook section and a loop section. 2) A foot strap with a hook section and a cooperating loop section fastener and two buckles to engage the one each of the adjusting straps on either side of the foot. Once adjusted, by moving the length of the adjusting straps equally, the user can walk with no fear of tripping.

Figure 1:
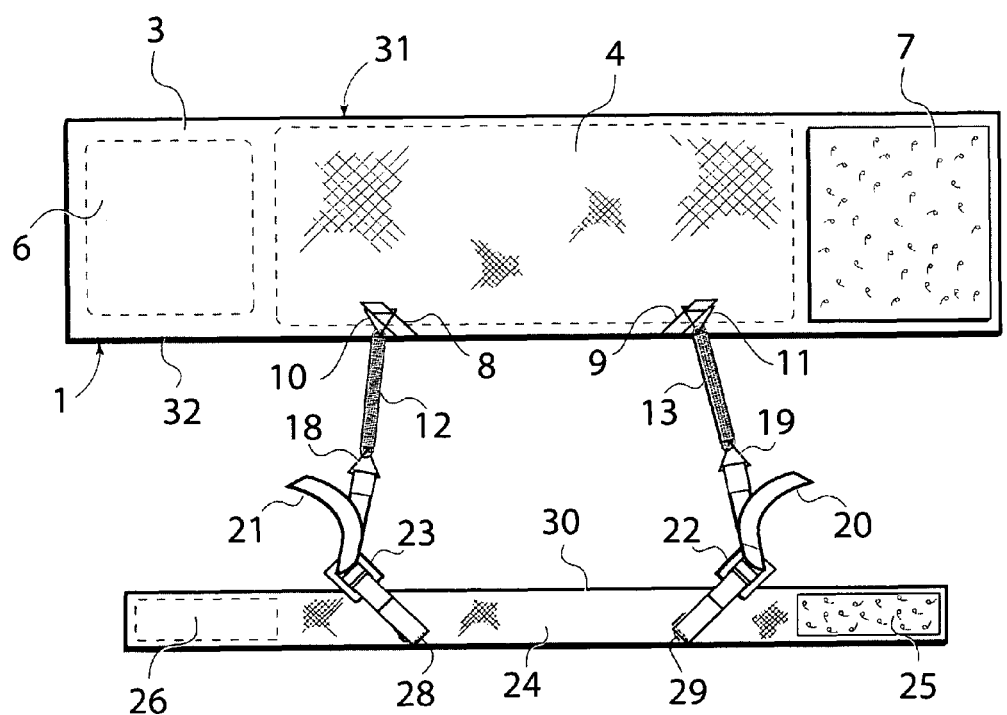
FIG. 1 is a front perspective view of one embodiment of a foot drop aid according the present invention.

In use the ankle belt 1 is position on the user's leg, inverted to the display in FIG. 1, such that the edge 31 is the lower edge of the ankle belt. The display in this manner provides a cleaner presentation of the components without overlaying them on the ankle belt.

Figure 2:
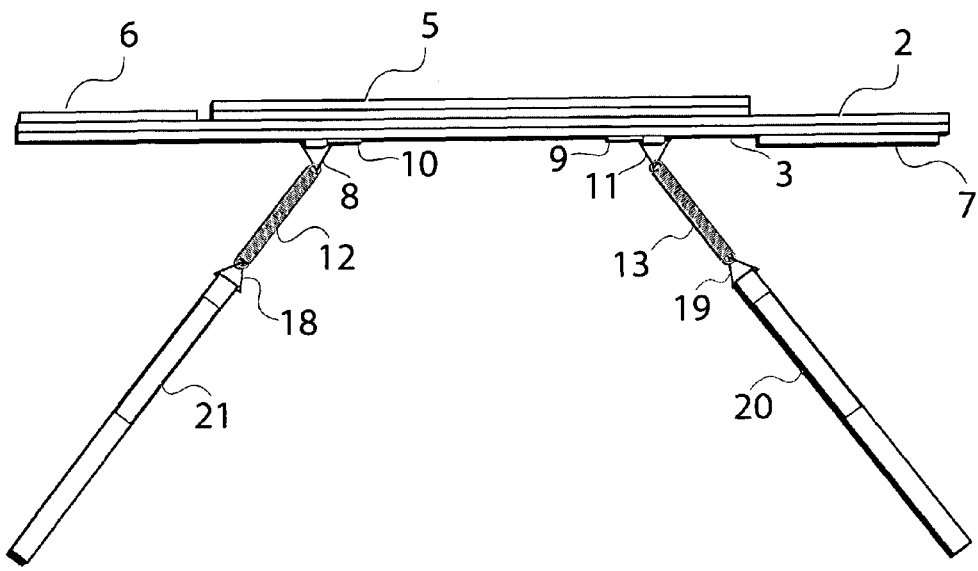
FIG. 2 is a side view of the foot drop aid of FIG. 1 showing hook material on one side of the ankle belt and loop material on the other side which cooperate to attach the ankle around the ankle of the user.

FIGS. 1 and 2 show the foot drop aid (FDA). The FDA comprises an ankle belt or cuff 1, which made of a stout cloth, such as denim, of two sheets or single sheet folded over to form a pocket to provide the inner sheet 2 and the outer sheet 3. A stiffener 4 shown by phantom lines is smaller than the denim sheets and positioned between the sheets, to extend over a portion of the center area of the belt to provide a semirigid structure in order to maintain the cloth as upright when positioned on the leg of a user. Although not shown, a single piece of cloth can be used as the belt with the stiffener attached as by sewing onto the belt with a foam pad attached over the stiffener. In use about the ankle of a user the longitude of the belt 1 is greater than the vertical height. The cloth has longitudinal flexibility, is comfortable and less likely to cause irritation on the leg and prevent the stiffener from contact with the skin. The stiffener may be wire or plastic mesh. To further protect the user a foam rubber sheet 5 is adhered to inner sheet 2 between the users leg and the cloth of the belt when the FDA is in use.

A hooks and loops attachment system (VELCO®) is provided on the belt 1 to hold it in place around the leg by attaching a hooks or loops component 6 at one end of the belt on inner sheet 2 and a cooperating component 7 (hooks or loops) at the distal end of the belt on outer sheet 3.

Figure 4:
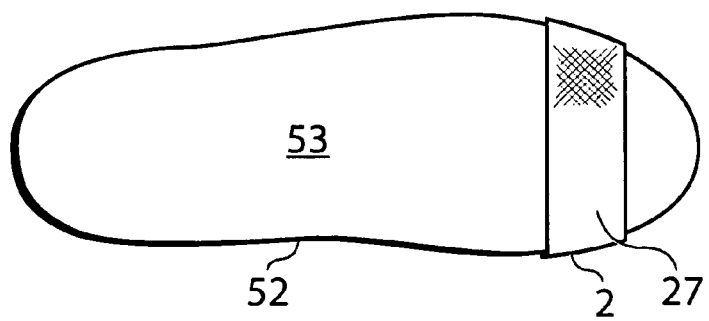
FIG. 4 is bottom view of a shoe showing a position of the shoe strap passing around the bottom of the shoe forward of the ball of the foot when the foot drop aid is in use as shown in FIGS. 3 and 5.

A pair of cloth tabs 8 and are spaced apart and attached adjacent to the upper edge 32 to each hold brackets 10 and 11, respectively, such as plastic or metal triangles or rings to which are attached to one end of coil springs 12 and 13, respectively. The distal end of each coil spring is attached by connectors 18 and 19, respectively to a pair of straps 21 and 20 each having cooperating hook and loop surfaces. The straps each pass through buckle 22 or 23, respectively and are releaseably engaged by the hooks and loops to thereby adjust the distance of the belt 24 from the ankle belt 1. Each buckle 22 and 23 is affixed by a strap to opposite ends of belt 24 by tabs 29 and 28, respectively. Tabs 28 and 29 are cloth sown onto cloth belt 24 and spaced apart to be on either side of the shoe or foot in use. At distal ends of the shoe/foot belt 24, cooperating hooks/loops 25/26 are positioned on opposite sides of the belt to the engage the belt around the shoe or foot such that the engagement of 25 and 26 is on the top of the shoe/foot and the continuous portion 27 of the belt 24 is on the bottom (see FIG. 4).

Figure 5:
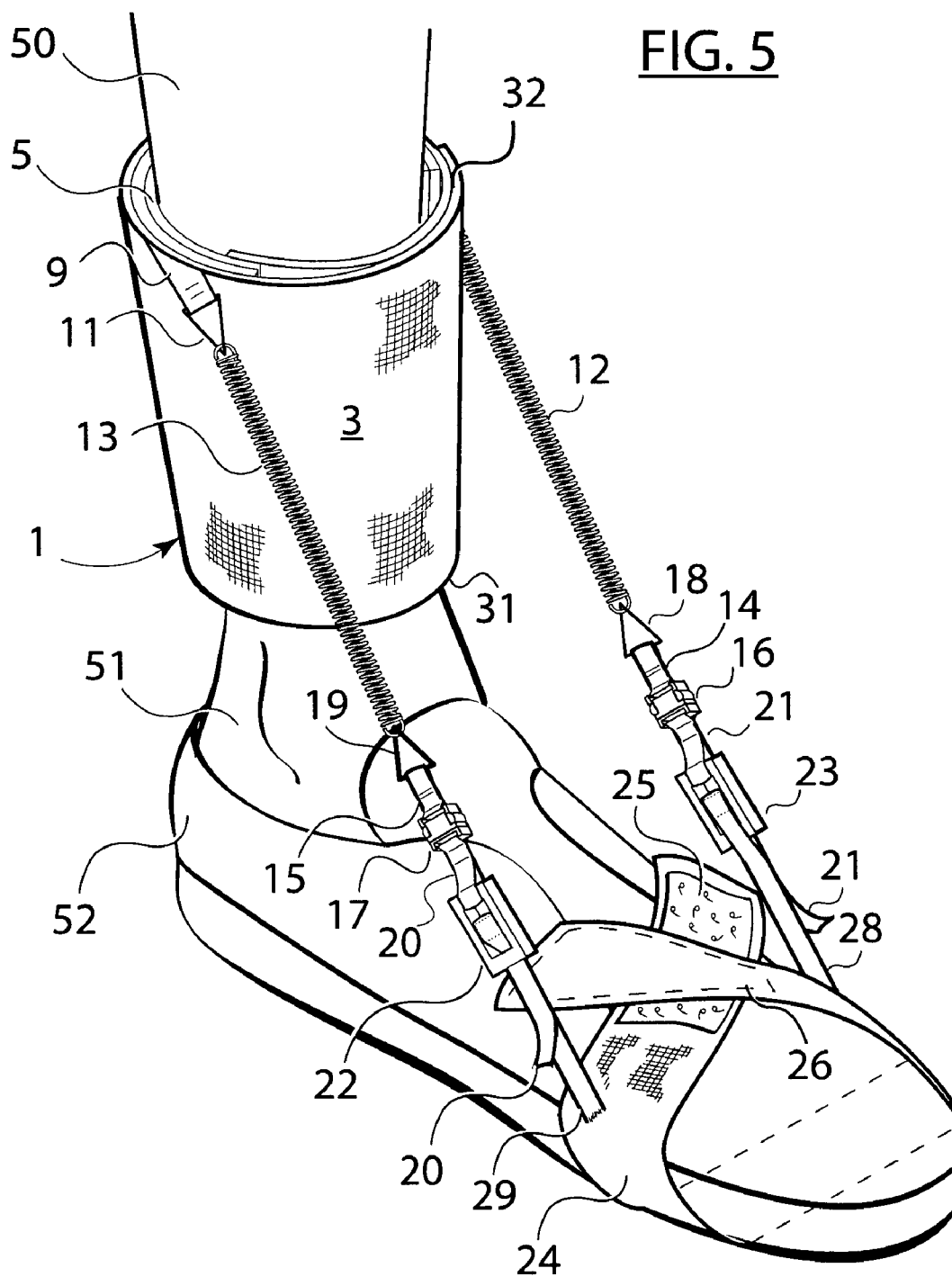
FIG. 5 is perspective view of an alternative version of a foot drop aid embodiment as viewed from the outside of a person's right leg shown in conjunction with a shoe on the person's foot.

An alternative means for connecting the ankle belt 1 to the belt 24 is shown in FIG. 5, where mechanical quick connect/disconnect latches 17 and 16 are inserted with straps 15 and 14 between buckle 22 and 23 and coil springs 13 and 12, respectively.

The major advantage of the present FDA compared to prior similar devices, is the spring action. It has been found that the elastomeric materials, lose the repeatability of the elastomeric lift very quickly thus become unuseable. In walking, the toe is only slightly elevated above the surface, and the lift must always reliably be the same or the user will trip and fall. As the leg goes forward, while walking, the heel contacts the ground, then the ankle bends so that the ball of the foot reaches the floor. This angle between the bottom of the foot and the shin is greater than 90 degrees and the springs stretch. As the step progresses to the rear (i.e., the user walks forward), the ankle again bends so that the heel rises with the ball of the foot still on the floor, with the angle less than 90 degrees at which point the springs relax. As the foot moves forward, the springs lift the foot to the proper position without dragging the toe and completing the step. The springs reliably repeat the mechanical action without any observed decline in the functionality over a sustained test period.

Figure 3:
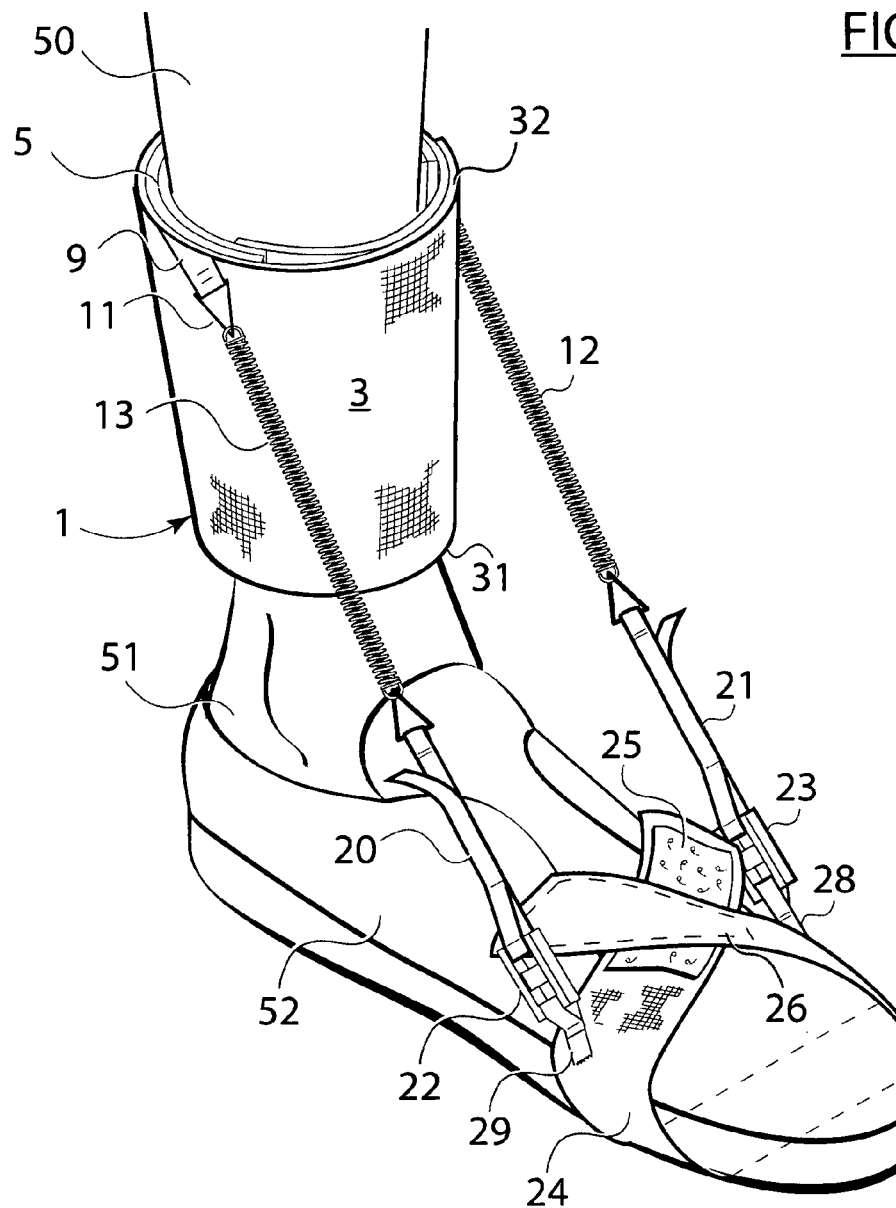
FIG. 3 is perspective view of the FIG. 1 embodiment as viewed from the outside of a person's right leg shown in conjunction with a shoe on the person's foot.

In order to fit the FDA on a user, as shown in FIGS. 3 and 5 the ankle belt is placed around the lower leg just above ankle bone, preferably over a sock or hose, since there may be repetitions of the mechanical process of foot lifting with a concurrent stress on the user's leg 50. The foam 5 goes against the ankle on the back side of the leg to provide further protection for the leg.

The ankle belt should rest just above the ankle bones (not shown) that stick out on either side of the foot 51. With the ankle belt securely fastened to the ankle, the belt is rotated, as required, about the ankle so that the springs are positioned on the left and right sides of the ankle.

The foot strap 24 is placed under the shoe 52. The foot strap, which may be a flexible ribbon like material, is positioned slightly forward of the ball (not shown) of the foot. The cooperating hooks and loops 25 and 26 on ends of foot strap, are crossed, each making a chevron over the top of the shoe or foot. Where the straps intersect, the sides of the shoe adjust them so that they conform to the shoe shape. This gives maximum comfort and creates a funnel that the shoe fits in when the strap is pulled back toward the ankle. Doing this, will also prevent a loop (not shown) forming on the bottom 53 of the sole that can catch on floor objects.

To adjust the foot lift, the spring straps 20 and 21 are passed through the buckles 22 and 23 respectively (FIG. 3) on the foot strap 24. The leg with the FDA is lifted so that the foot is off the floor. The intention is to adjust both straps at the same time so that the foot is held 90 degrees to the shin (not shown). The foot is now lifted and held in place by the extended springs. The FDA can be used on sandals, shoes with no heels or with moderate heels. Using a barefoot pad (not shown) under the foot lift can then be worn with covered bare feet, typically at night or around the home.

The toes of the foot will not drag on the floor. Should the toes be too low and drag on the floor or the foot strap drags on the floor due to a loop under the shoe, the straps should be readjusted until the springs hold the foot higher. The foot at the beginning and end of the step will flex, due to the springs, and still return to lift the foot. This is how the FDA allows for normal walking and requires no special adaptation be made to the shoe.

While there has been described what is presently believed to be the preferred embodiment of the invention, those skilled in the art will realize that changes and modifications may be made thereto without departing from the spirit of the invention, and it is intended to claim all such changes and modifications as fall within the true scope of the invention.

The invention claimed is:

1. An orthotic lift apparatus comprising:
a first belt having two ends, a hooks/loops component on a first side at a first end of said first belt and a cooperating hooks/loops component on a second side of said first belt distal to said first end;
a pair of first brackets spaced apart and attached to said first side of said first belt, and a pair of coil springs attached to each of said first brackets;
a second belt having two ends, a hooks/loops component on a first side of said second belt at a first end and a cooperating hooks/loops component on a second side of said second belt distal to said first end;
a pair of second brackets spaced apart and attached to one side of said second belt; and
two adjustable, releaseable straps attached one each to said springs and attached one each to said second brackets in operable alignment with one each said springs.

2. The orthotic lift apparatus according to claim 1 wherein said first belt is an ankle member and said second belt is a shoe/foot member.

3. The orthotic lift apparatus according to claim 1 wherein said adjustable, releaseable straps have hook and loops cooperating components for both adjustment and release.

4. The orthotic lift apparatus according to claim 1 wherein said adjustable, releaseable straps have a mechanical release therein.

5. The orthotic lift apparatus according to claim 1 wherein said first belt is flexible along a longitudinal axis and semi-rigid along a vertical axis, said vertical axis being shorter than said longitudinal axis.

6. The orthotic lift apparatus according to claim 5 wherein said first belt is form of cloth and a stiffening member is incorporated therewith.

7. The orthotic lift apparatus according to claim 1 wherein a foam pad is attached on said second side of said first belt.

8. The orthotic lift apparatus according to claim 1 wherein said second belt is a flexible ribbon.

9. The orthotic lift apparatus according to claim 2 wherein said adjustable, releaseable straps have hook and loops cooperating components for both adjustment and release.

10. The orthotic lift apparatus according to claim 9 wherein said adjustable, releaseable straps have a mechanical release therein.

11. The orthotic lift apparatus according to claim 10 wherein
said first belt is flexible along a longitudinal axis and semi-rigid along a vertical axis, said vertical axis being shorter than said longitudinal axis.

12. The orthotic lift apparatus according to claim 11 wherein
said first belt is form of cloth and a stiffening member is incorporated therewith.

13. The orthotic lift apparatus according to claim 12 wherein
a foam pad is attached on said second side of said first belt.

14. The orthotic lift apparatus according to claim 13 wherein
said second belt is a flexible ribbon.

15. A foot lift apparatus comprising:
a first belt adapted to be about lower leg having two ends, a hooks/loops component on a first side at a first end of said first belt and a cooperating hooks/loops component on a second side of said first belt distal to said first end;
a pair of first brackets spaced apart and attached to said first side of said first belt and adapted to be one on each side of a lower leg, and a pair of coil springs attached to one each of said first brackets;
a second belt adapted to be positioned about a shoe/foot just forward the ball of a foot, having two ends, a hooks/loops component on a first side of said second belt at a first end and a cooperating hooks/loops component on a second side of said second belt distal to said first end;
a pair of second brackets spaced apart and attached to one side of said second belt; and
two adjustable, releaseable straps attached one each to said springs and attached one each to said second brackets in operable alignment with one each said springs.

16. The foot lift apparatus according to claim 15 wherein said adjustable, releaseable straps have hook and loops cooperating components for both adjustment and release.

17. The foot lift apparatus according to claim 16 wherein said adjustable, releaseable straps have a mechanical release therein.

18. The foot lift apparatus according to claim 17 wherein said first belt is flexible along a longitudinal axis and semi-rigid along a vertical axis, said vertical axis being shorter than said longitudinal axis.

19. The foot lift apparatus according to claim 18 wherein said first belt is form of cloth and a stiffening member is incorporated therewith.

20. The foot lift apparatus according to claim 19 wherein a foam pad is attached on said second side of said first belt and said second belt is a flexible ribbon.

21. A lift assist apparatus to alleviate focal limb weakness, comprising:
a first belt having a first end and a second end, said first and second ends arranged and designed to releasably attach so that said first belt forms a loop;
a second belt having a first end and a second end, said first and second ends arranged and designed to releasably attach so that said second belt forms a loop;

a pair of first brackets spaced apart and attached to said first belt, and a pair of second brackets spaced apart and attached to said second belt;

a pair of adjustable straps attached one each to said first brackets or said second brackets; and a pair of springs having opposing ends, each of said springs attached at one end to one of said adjustable straps and at an opposing end to one of said first or second brackets.

* * * * *